(12) United States Patent
Hoernig (10) Patent No.: US 7,656,993 B2
(45) Date of Patent: Feb. 2, 2010

(54) COMPRESSION DEVICE AND METHOD FOR ADJUSTMENT OF A COMPRESSION PRESSURE

(75) Inventor: Mathias Hoernig, Erlengen (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 11/834,811

(22) Filed: Aug. 7, 2007

(65) Prior Publication Data
US 2008/0043904 A1 Feb. 21, 2008

(30) Foreign Application Priority Data
Aug. 16, 2006 (DE) .................. 10 2006 038 163

(51) Int. Cl.
*A61B 6/04* (2006.01)
(52) U.S. Cl. .................. 378/37; 378/208; 128/845
(58) Field of Classification Search .................. 378/37, 378/204, 208, 210; 128/845
See application file for complete search history.

(56) References Cited

U.S. PATENT DOCUMENTS

| 6,128,523 | A | 10/2000 | Bechtold et al. | |
|---|---|---|---|---|
| 6,500,119 | B1* | 12/2002 | West et al. | 600/437 |
| 6,587,578 | B2* | 7/2003 | Godik et al. | 382/128 |
| 6,746,400 | B2* | 6/2004 | Rathjen | 600/405 |
| 2004/0202280 | A1* | 10/2004 | Besson | 378/37 |
| 2004/0236194 | A1* | 11/2004 | Meyer | 600/302 |
| 2005/0113683 | A1 | 5/2005 | Lokhandwalla et al. | |
| 2005/0271403 | A1* | 12/2005 | Kaneko et al. | 399/44 |
| 2007/0223652 | A1* | 9/2007 | Galkin | 378/37 |
| 2008/0115844 | A1* | 5/2008 | Teichmann et al. | 137/557 |
| 2009/0175408 | A1* | 7/2009 | Goodsitt et al. | 378/37 |
| 2009/0213986 | A1* | 8/2009 | Thaler | 378/37 |

FOREIGN PATENT DOCUMENTS

DE 10 2004 017 849 A1 12/2004
WO WO 2006/048269 * 5/2006

* cited by examiner

Primary Examiner—Edward J Glick
Assistant Examiner—Mona M Sanei
(74) Attorney, Agent, or Firm—Schiff Hardin LLP (57) ABSTRACT

A compression device has a compression plate that applies a pressure to a subject on a support plate. The compression plate has a number of elastically-deformable compression plate elements that are substantially transparent for an examination field used with the compression device. In a method for compressing a subject, at least one pressure sensor measures the pressure applied by a compression device to a subject, and wirelessly supplies a signal representing the detected pressure to a control unit, wherein the detected pressure is compared to a stored compression pressure value. The control device adjusts the pressure applied to the subject by the compression device so that the pressure detected by the sensor is equal to the stored compression pressure value.

19 Claims, 4 Drawing Sheets

COMPRESSION DEVICE AND METHOD FOR ADJUSTMENT OF A COMPRESSION PRESSURE

BACKGROUND OF THE INVENTION

1. Field of the Invention

The present invention concerns a compression device and a method for adjustment of a compression pressure.

2. Description of the Prior Art

Compression devices are used in many technical fields in which it is necessary, for example, to compress an object or a number of objects, to adjust the thickness of an object, or to seal a leak of an object. Possible technical fields are, among other things, material sciences, food monitoring and medical technology.

Compression devices are used in the medical field in, among other things, mammography and for biopsy procedures. A compression device normally has a compression plate provided for compression of the subject to be examined (the female breast in the case of mammography). Today the compression is normally implemented with rigid, inflexible compression plates. The compression device together with the rigid compression plate is displaced relative to a bearing table on which the subject to be examined or to be compressed is supported. In mammography the compression by means of a rigid compression plate often causes pain in the breast during the compression.

By having a large number of differently-shaped rigid compression plates available, which are respectively adapted to different sizes and shapes of female breasts, it is sought to be able to select and prepare a compression plate best adapted for a specific patient.

The compression serves to reduce the breast tissue to be x-rayed in terms of its thickness in the case of mammography with x-rays, so scatter rays are reduced, as well as causing the breast to be more spaced from the thorax during the examination, so a surface-proximal examination of the breast is enabled.

SUMMARY OF THE INVENTION

An object of the present invention is based on the object to provide a compression device which allows a compression of a subject to be compressed under consideration of its physical structure.

This object is achieved in accordance with the invention by a compression device with a compression plate that exhibits a number of elastically-deformable compression plate elements that are essentially transparent for the examination field that at least partially penetrates the compression plate elements.

By using a number of elastically-deformable compression plate elements, the physical structure of the subject to be compressed can be better accommodated. "A number of compression plate elements" means at least two compression plate elements. The number of compression plate elements can be moved relative to one another, so the compression plate can adapt to a shape of a subject. Furthermore, the compression plate elements can be coupled with one another with coupling components. The shape of the compression plate elements that can be set (selected) arbitrarily. A good adaptation of the shape of the compression plate to that of the respective contour of the subject to be compressed, such as the anatomy of a female breast, can be achieved during the compression of the subject to be compressed by the multiple elastically-deformable compression plate elements.

The compression plate can have a selected surface region adapted to the subject to be compressed, the surface region being formed by the multiple elastically-deformable compression plate elements. Alternatively, the entire compression plate can be formed by the multiple elastically-deformable compression plate elements.

In an embodiment of the invention, at least one compression plate element is fashioned as a tube-shaped body. A tube-shaped formation of the compression plate elements provides a cost-effective way to adapt the compression plate to the anatomy of the subject to be compressed. All compression plate elements can be fashioned as tube-shaped bodies. The individual tube-shaped compression plate elements are arranged in a relaxed state (i.e. in a state not compressing the subject to be compressed), along the horizontal primary inertial axis of the subject to be compressed (for example a female breast of a standing patient). Alternatively, compression plate elements that are band-shaped can also be used.

For compression of a female breast of a patient, the tube-shaped compression plate elements of the compression plate can be oriented essentially horizontally and essentially perpendicularly to a surface normal of the sternum of the patient, or essentially horizontally and essentially parallel to the surface normal of the sternum of the patient. This is applicable both for a horizontal and for a vertical positioning of the patient during a compression of a subject to be compressed.

The alignment of the compression plate elements along the primary inertial axes of inanimate subjects to be compressed can likewise ensue.

Individual tube-shaped compression plate elements can exhibit varying elastic properties dependent on their position within the compression plate. For example, in the case of a female breast a horizontal converter element positioned perpendicularly to the surface normal of the sternum of patient and closer to the thorax of the patient can exhibit a lower spring constant, or the magnitude of the modulus or elasticity for this compression plate can be smaller than for a compression plate element situated further removed from the chest of the patient with an essentially identical orientation, in order to provide a maximum compression force on the subject to be compressed.

In a further embodiment of the invention, at least one compression plate element is fashioned as a solid cylindrical body. All compression plate elements that are in contact with the subject to be compressed during the compression thereof are advantageously fashioned as solid-cylindrical bodies. Different elasticity properties, in particular spring constants or moduli of elasticity, can be set for different compression plates by the use of different materials for the compression plate elements fashioned as solid cylinders.

In another embodiment of the invention, at least one compression plate element is fashioned as a hollow-cylindrical body. All compression plate elements that are in contact with the subject to be compressed during the compression thereof are advantageously fashioned as hollow-cylindrical bodies. The elastic properties (in particular the spring constant or modulus of the elasticity) of individual compression plate elements can be set by filling the hollow-cylindrical compression plate elements with a gas and/or a fluid. A further improvement is that the pressure of the gas that is present in the respective compression plate element and/or the pressure of the fluid present in the respective compression plate element can be variably adjusted, possibly controlled with a control device.

Alternatively, a combination of variously-fashioned compression plate elements is also possible, for example a combination of compression plate elements fashioned as hollow cylinders, solid cylinders, mosaic-like elements or band-like elements.

In a further advantageous embodiment of the invention, at least one compression plate element is produced from a material having material properties that do not change significantly due to an interaction with the examination field. A long service life of the compression plate elements is made possible due to the constancy of the material properties of the material used for all compression plate elements, for example for x-rays as the examination field. Furthermore, the inventive compression device has the advantage that, in the case of a defect, individual compression plate elements can be exchanged and the entire compression plate does not need to be replaced (as with conventional rigid compression plates).

The materials used can be advantageously selected not only with regard to an invariability of the material properties over a long time span but also with regard to the use of a particular examination field. If, for instance, x-rays are used as the examination field, it is appropriate that the materials used for the compression plate have a high transparency for x-rays in order to not significantly impair the examination success. This analogously applies for other examination fields (such as ultrasound waves, medical facilities, particle beams, gamma rays, light in the visible spectrum, etc.) to be used for an examination.

The material to be used for the compression plate elements is advantageously plastic. Polyvinylchloride, various polyurethanes as well as Caoutchouc derivatives (in particular rubber) appear particularly suitable for the use of x-rays. An advantage of these materials is that they are formed by long-chain molecules, and the elements from which the molecule is composed exhibit a low atomic mass. A low absorption of x-rays thus occurs, for example with regard to an examination by means of x-rays. Furthermore, plastics can be produced and processed in a simple manner. Arbitrary shapes (forms) can be cost-effectively provided for a compression plate element, for example band shapes, tube shapes, films, etc.

In an embodiment of the invention at least one compression plate element has at least one sensor for measurement of the compression pressure on a subject to be compressed. The compression pressure on the subject to be compressed can be detected directly at the compressed subject during the compression by means of at least one sensor for measurement of the compression pressure. Monitoring of the compression pressure on the subject to be compressed can thereby ensue. A sensor for measurement of a compression pressure advantageously has a surface of one square millimeter or less in order to not adversely affect the examination to be implemented. A number of sensors for measurement of the compression pressure is advantageously present in order to enable better monitoring of the compression pressure on the subject.

In a further embodiment of the invention, at least one sensor for measurement of the compression pressure has at least one component for contact-free transfer of data and/or energy. By a contact-free transfer of data and/or energy from or to the sensor, no cabling of the sensors is required, so that the freedom of movement of the compression plate is not limited by the need for transfer of data and/or energy.

Furthermore, the use of examination fields such as, for example, x-rays, is distinctly less limited by a contact-free operation of the sensor than given the use of metallic cabling, which leads from a sensor to, for example, a control device. The transfer of energy for operation of the sensor represents no technical difficulty for the provided sensors for measurement of a compression pressure.

X-rays, particle beams, gamma rays, ultrasound, medical facilities and further examination fields used in medicine, in the material sciences, in food monitoring and further means which can serve for examination or analysis and treatment of subjects are possible as the examination field.

At least one sensor for measurement of the compression pressure advantageously is a piezoelectric element. Piezoelectric elements can advantageously be used as a sensor for measurement of the compression since pressure sensors with small spatial dimensions can be realized by such piezoelectric elements. Piezoelectric elements are additionally cost-effective since they are available as bulk commodities. A number of sensors for measurement of the compression pressure thus can be provided without great technical or financial expenditure, which increases the safety of the subject to be compressed.

Alternatively, at least one sensor for measurement of the compression pressure has a pyroelectric element. The compression pressure on the subject to be compressed, in particular a living, heat-emitting subject, can in particular be detected indirectly by the use of a number of pyroelectric elements. The more that a subject to be compressed (in particular a female breast) is compressed, the greater the contact surface of the subject with the compression plate.

If the subject to be compressed comes incrementally into contact with the compression plate during the compression, heat is transferred via the contact surface from the subject to be compressed onto the compression plate or onto the compression plate elements. The heating of the compression plate can be detected as an electrical signal by means of the pyroelectric elements. The distribution of the heat on the compression plate is thus a measure for the compression of the subject to be compressed.

In another embodiment of the invention, a number of sensors are provided for measurement of the compression pressure on the subject to be compressed, and the sensors exhibit various positions and/or orientations on at least one compression plate element. A compression pressure distribution for the subject to be compressed can be determined by the arrangement of the sensors at different positions and/or orientations on at least one compression plate element for measurement of the compression pressure on the subject to be compressed. The multiple sensors are advantageously distributed across the multiple compression plate elements. This allows a monitoring of the compression of the subject to be compressed.

In a further embodiment of the invention, the compression pressure can be adjusted to the subject to be compressed by changing a tension state of at least one compression plate element. The spring constant or the modulus of elasticity for the respective compression plate element can be adjusted by the adjustment of the tension state of the compression plate elements. The adjustment can ensue by a tightening or loosening of a (for example tube-shaped) compression plate element, i.e. via a length alteration of the compression plate element active for the compression. Alternatively, for example, the tension state can be altered by adjusting the spring constant of the compression plate element, for example, by an alteration of a gas pressure or fluid pressure inside the compression plate element. The compression plate can thereby be even better adjusted to the physical structure of the subject or, respectively, the anatomy of a patient to be compressed. The adjustment of the tension state of the compression plate elements can, for example, ensue controlled by a control device.

For example, a value for a compression pressure which should advantageously be reached and which may not be exceeded is stored in the control device for controlling the compression device or the compression pressure on the subject to be compressed. The control tensions at least one compression plate element such that the compression pressure or compression pressure value detected with at least one sensor for measurement of the compression pressure essentially coincides with the value for the compression pressure stored in the control device.

An automated adjustment of the compression pressure on a subject to be compressed is possible for those embodiments of the invention that employ at least one sensor for measurement of a compression pressure and that enable an adjustment of the compression pressure, for example by an alteration of the fluid pressure or a gas pressure in at least one compression plate element fashioned as a hollow cylinder, by displacement of the compression plate relative to the support table, by shortening and lengthening of the compression plate elements that are active for compression of the compressed subject, etc.

A further object of the invention is to provide a method that allows a compression of a subject to be compressed dependent on its physical structure.

This object is inventively achieved by a method for adjustment of a compression pressure, wherein the compression pressure on a subject to be compressed is detected with at least one sensor for measurement of the compression pressure on the compressed subject; wherein a compression pressure value associated with the detected compression pressure is supplied without contact to a control device. The compression pressure value supplied to the control device is compared with a compression pressure value stored in the control device. The compression pressure on the subject to be compressed is adjusted such that the compression pressure value associated with the compression pressure detected by the at least one sensor for measurement of the compression pressure is equal to that compression pressure value stored in the control device.

By such a method, compression of the subject to be compressed can be provided, with the anatomy of the subject to be compressed being taken into account. "Compression pressure value" means data that can be unambiguously associated with a compression pressure, and vice versa. A compression pressure value can include information about positions of the sensors detecting the compression pressure, the magnitude of the measured compression pressure, measurement points in time, etc.

In an embodiment of the inventive method the compression pressure is detected at periodic time intervals by the at least one pressure sensor. It is thereby ensured that the compression pressure cannot be increased significantly beyond a predeterminable limit value insofar as the time intervals are selected small enough. The time intervals between the measurement of a first compression pressure and a directly subsequent measurement of a second compression pressure are appropriately adapted depending on the level of a compression range. Alternatively, a sufficiently high measurement frequency for the compression pressure can be selected from the beginning.

It is likewise appropriate to increase the measurement frequency for detection of the compression pressure by means of the respective sensor near to the predetermined adjustable limit value, in order to prevent exceeding limit value given increasing compression of the subject to be compressed. The examination result is improved and an increased safety for the subject to be compressed is achieved by the monitored compression.

In a further embodiment of the inventive method the compression pressure on the subject is adjusted by an actuation device controlled by the control device. The control device controls, for example, the displacement of the compression plate relative to the support table, the tension state of compression plate elements, or the gas or fluid pressure in compression plate elements fashioned as hollow cylinders. The greater the number of sensors that is selected for measurement of the compression pressure (these exhibiting different positions and/or orientations on the compression plate), the more safely that conclusions can be made about the distribution of the pressure on the subject.

Furthermore it is advantageous to include the step of manually adjusting at least one compression pressure value that is stored in the control device. This predeterminable limit value of the compression pressure which should not be exceeded can be adapted according to the subjective pain sensitivity of a patient. Patients can alternatively be classified according to pain classes, and a specific compression pressure value for the compression to be implemented (which compression pressure value should not be exceeded) can be associated with each pain class. The classification of the patient in one of the pain classes can ensue, for example, through questioning or by a pain test of the patient.

The stored compression pressure value can be quickly and individually established after a classification of the patient in a pain class. The maximum compression pressure value to be reached is set through a correct association of a pain class (for example for a female patient), such that the compression of the female breast is at no point in time perceived by the woman to be uncomfortable to an excessive extent.

In an embodiment of the inventive method a compression pressure distribution of the subject to be compressed is determined during the compression from the compression pressures detected for the subject to be compressed by a number of sensors arranged at different positions and/or in different orientations on at least one compression plate element. A pressure distribution for the subject to be compressed can be determined using the compression pressures detected by these sensors. With the use of multiple pressure sensors, a sufficient spatial resolution can be achieved in order to be able to make diagnostic conclusions with regard to a local or global pressure maximum that results, for example, from the presence of a nodule in a female breast. To improve the spatial resolution of this method, interpolation methods can be used.

The compression pressure distribution for the subject to be compressed is advantageously graphically represented at a display device. A color coding of the compression pressure detected with the sensors for representation of the compression pressure distribution on the subject is advantageous in order to allow the maximum of the pressure on the subject to be quickly recognized.

DESCRIPTION OF THE PREFERRED EMBODIMENTS

Figure 1:
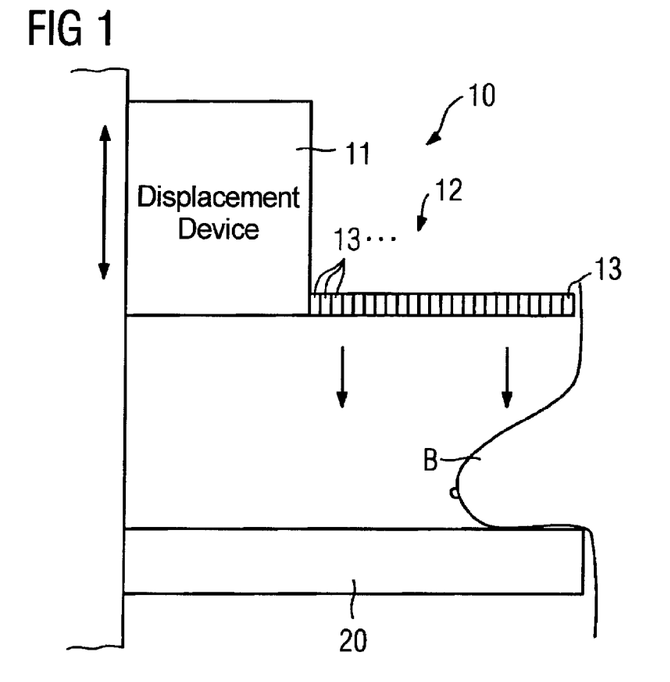
FIG. 1 is a side view of a female breast on a support table with an inventive compression device in a state not compressing the female breast.

FIG. 1 shows a side view of a compression device 10 that includes a displacement device 11 and a compression plate 12. Additionally shown is a support table 20 on which is arranged a subject B to be compressed. The subject B to be compressed in FIG. 1 is a female breast of an examination subject. FIG. 1 shows an arrangement for compression of the female breast B, the breast B being arranged between the compression plate 12 and support table 20.

The compression device 10 can be displaced in the vertical direction relative to the support table 20. Decreasing the spacing between the compression plate 12 and the support table 20 can be achieved by a displacement of the displacement device 11 together with the compression plate 12 relative to the support 20. At a certain distance (predetermined by the anatomy of the breast B), the surface of the breast B is contacted and compressed with the compression plate 12 upon further displacement of the displacement device 11 together with the compression plate 12 in the direction of the support table 20. In FIG. 1 the compression plate 12 has a number of elastically-deformable compression plate elements 13 that come into contact with the breast B and press on the breast B little by little upon the displacement of the compression plate 12 in the direction of the support table 20.

In contrast to known compression devices, the compression plate 12 can be displaced down to the support table 20 by the inventive compression device 10. The elastically-deformable compression plate elements 13 produce a compression force dependent on deflection thereof by the subject B to be compressed and the spring constant of each compression plate element 13. A uniform compression of the breast B, that is not possible in the case of conventional, essentially inelastic compression plates, is achieved by the gradual adaptation of the compression plate elements 13 to the anatomy of the breast B.

Figure 2:
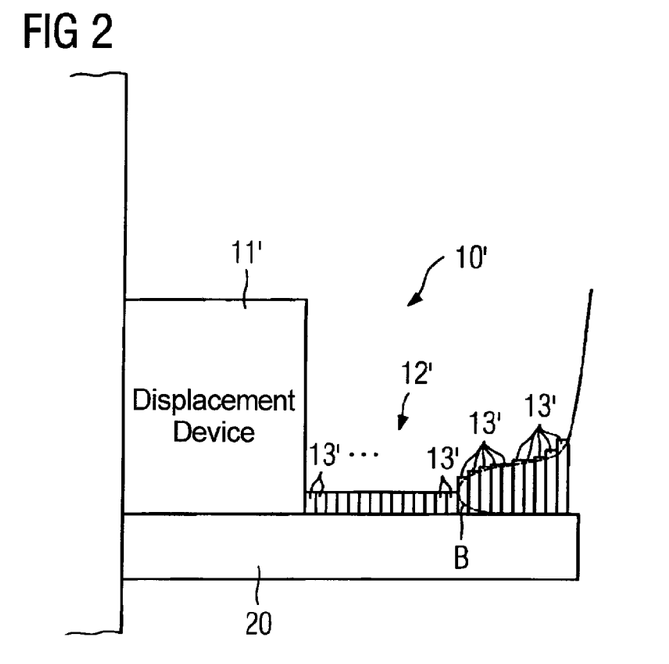
FIG. 2 is a side view of a female breast on a support table with an inventive compression device in a state compressing the female breast.

A compression device 10' in the compressing state is shown in FIG. 2, wherein the female breast B is compressed. The female breast B is compressed by a number of tube-shaped compression plate elements 13'. The width of the tube-shaped compression plate elements 13' can be varied nearly arbitrarily. Small tube widths are advantageously used so that the compression plates 12' can be used for a number of differing breast anatomies. The compression plate elements 13' are advantageously elastically coupled among one another with adjacent compression plate elements 13'.

Mosaic-like compression plate elements 13' also can be used due to the elastic coupling of compression plate elements 13', in particular compression plate elements 13' abutting one another. The use of elastically deformable compression plate elements 13' causes the required compression of the breast B to be perceived by the woman as more comfortable—less pain occurs due to the more uniform pressure of the breast B. An inventive compression device 10 according to FIG. 1 or 10' according to FIG. 2 is additionally more cost-effective than compression devices available today.

Figure 3:
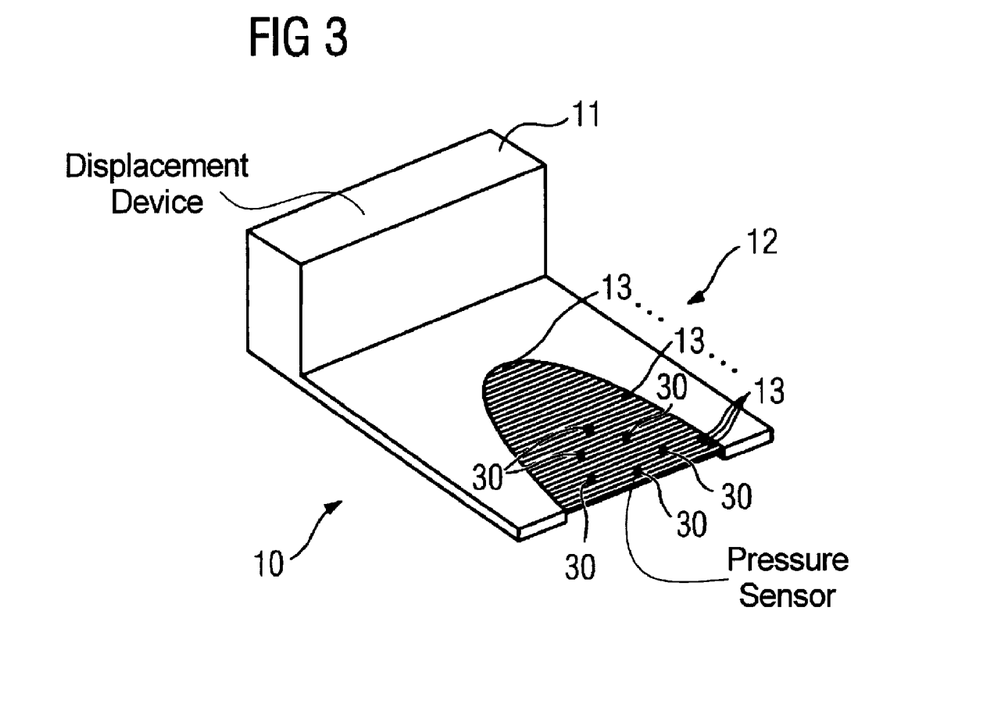
FIG. 3 is a perspective view of an inventive compression device in a non-compressing state.

FIG. 3 shows a compression device 10 in a non-compressing state. The compression device 10 has a displacement device 11 as well as a compression plate 12. In FIG. 3 the compression plate 12 is fashioned partially rigid (for instance made from polymethylmethacrylate (PMMA)), and is partially composed of elastically-deformable compression plate elements 13. The arrangement of the elastically-deformable compression plate elements 13 can be adapted to an arbitrary usage purpose of the compression itself or to the subject to be compressed. The arrangement of the compression plate elements 13 is shown in FIG. 3 as a half-ellipse. The arrangement of the compression plate elements 13 is mirror-symmetric relative to the semi-major axis of the ellipse, which forms an axis of mirror symmetry of the flat region of the compression plate 12 provided with the compression plate elements 13. The arrangement of the elastically-deformable compression plate elements 13 is thereby adapted to the subject, for instance to the compressed female breast B.

The compression plate elements 13 (fashioned as solid-cylindrical bodies) in FIG. 3 are oriented parallel to the leading edge of the compression plate 12. This direction essentially coincides with the primary axis of inertia of the female breast, which axis proceeds horizontally and perpendicularly to the surface normal of the sternum (not shown). An adaptation of the shape of the individual compression plate elements 13 to the anatomy of the female breast thus can be achieved in a particularly advantageous manner.

The compression plate elements 13 can be arranged according to FIG 3, meaning that the compression plate 12 has an essentially rigid part (for instance made from PMMA) on which multiple elastically-deformable compression plate elements 13 are carried. The essentially rigid part of the compression plate 12 can serve as a frame for arrangement of the multiple elastically-deformable compression plate elements 13. Alternatively, the entire compression plate 12 can be formed by the elastically-deformable compression plate elements 13.

FIG. 3 additionally shows a number of sensors 30 for measurement of the compression pressure of the compression plate elements 13 on the subject (female breast B). In the exemplary embodiment, the sensors 30 use piezoelectric elements in order to measure the pressure on the female breast B at the respective sensor position (FIG. 2). A compression pressure distribution of the female breast can be determined by the multiple sensors 30, which are arranged at different positions of the compression plate 12. The sensors 30 are advantageously positioned within the compression plate elements 13, each fashioned as a solid-cylindrical body.

Figure 4:
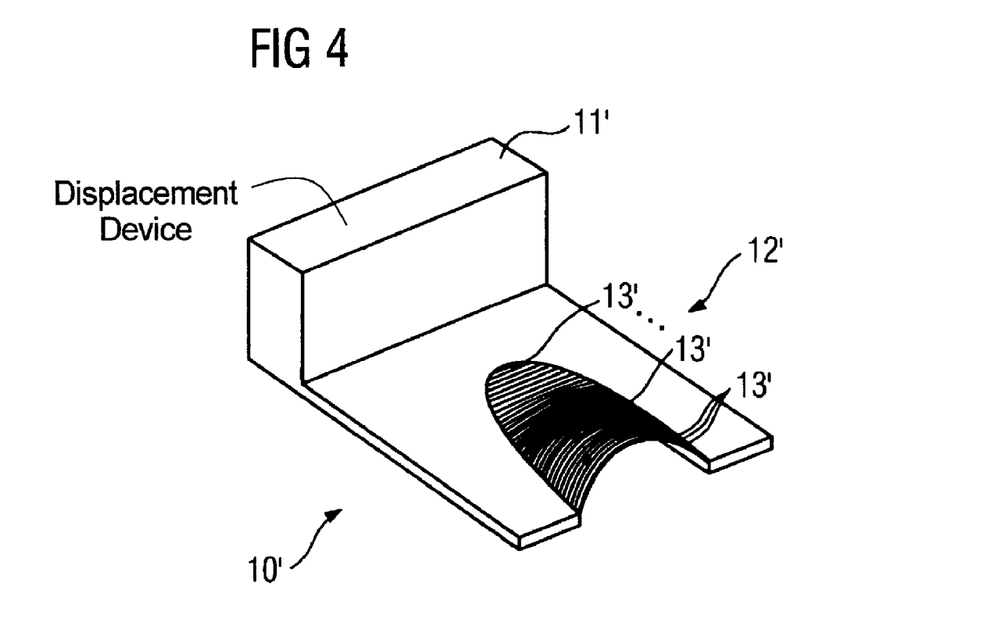
FIG. 4 is a perspective view of an inventive compression device in a compressing state.

FIG. 4 shows a compression device 10' in a state compressing a breast (not shown). Corresponding to the anatomy of the breast, on the patient side the compression plate elements 13' positioned at the edge of the compression plate 12' are more strongly deflected (relative to the rest position of the compression plate element 13 according to FIG. 3) than compression plate elements 13' centrally positioned on the compression plate 12'.

The elastically-deformable compression plate elements 13' generate a counterforce on the breast (not shown) according to their elastic properties, in particular their spring constant, and the deflection caused by the anatomy of the breast, which counterforce leads to a compression of the breast. The counterforce or the compression pressure on the breast is directly detected at the breast by the multiple sensors 30 at different positions. If applicable, an adjustment of the compression pressure on the breast can ensue for one compression plate element 13' or a number of compression plate elements 13' using the compression pressure measured with the sensors 30.

Figure 5:
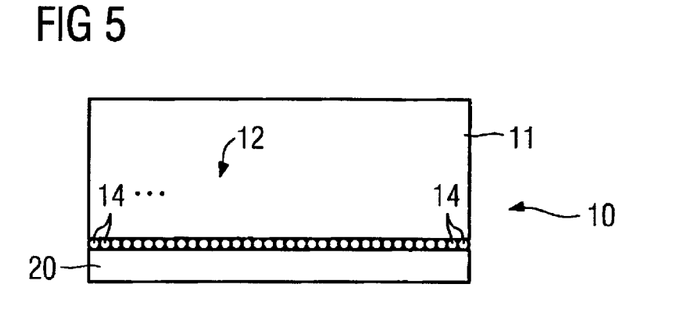
FIG. 5 is a front view for an inventive compression plate in a non-compressing state.

FIG. 5 shows a front view of an alternative embodiment for an inventive compression device 10 in a state not compressing a breast. The compression device 10 has a displacement device 11 and a compression plate 12 which is entirely assembled from a number of elastically-deformable compression plate elements 14. The compression plate elements 14 in FIG. 5 are rotated by 90 degrees relative to the previously shown compression plate elements 13 and 13' in FIG. 3 and FIG. 4. The compression plate elements 14 are fashioned as tube-shaped bodies and lie essentially parallel to a surface normal of the sternum of a patient (not shown) to be examined. In FIG. 5 the compression device 10 is arranged on a support table 20.

Figure 6:
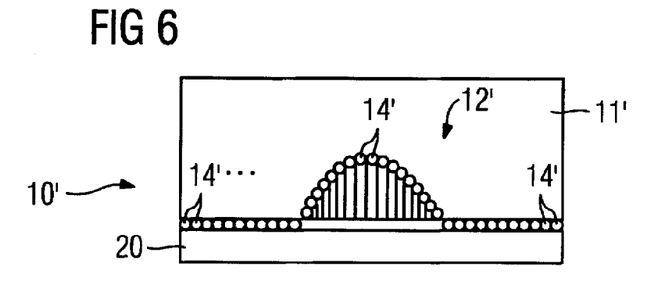
FIG. 6 is a front view for an inventive compression plate in a compressing state.

A front view of a compression device 10' in a state compressing a breast is shown in FIG. 6. This the arrangement is modified compared to the arrangement shown in FIG. 5 by the displacement device 11' together with the compression plate 12' being raised relative to the support table 20, the subject to be compressed (not shown in FIG. 6) being arranged on the support table 20, and the displacement device 11' together with the compression plate 12' is lowered in the direction of the support table 20. Due to the physical structure of the subject to be compressed, the compression plate elements 14' coming into contact with the subject to be compressed experience a deflection. The compression plate elements 14' are advantageously elastically coupled with adjacent compression plate elements 14' perpendicular to their orientation. The subject to be compressed is compressed by further displacement of the compression plate 12' in the direction of the support table 20. Here as well sensors (not shown in FIG. 6) for measurement of the compression pressure on the subject in the compressed state can be provided.

Figure 7:
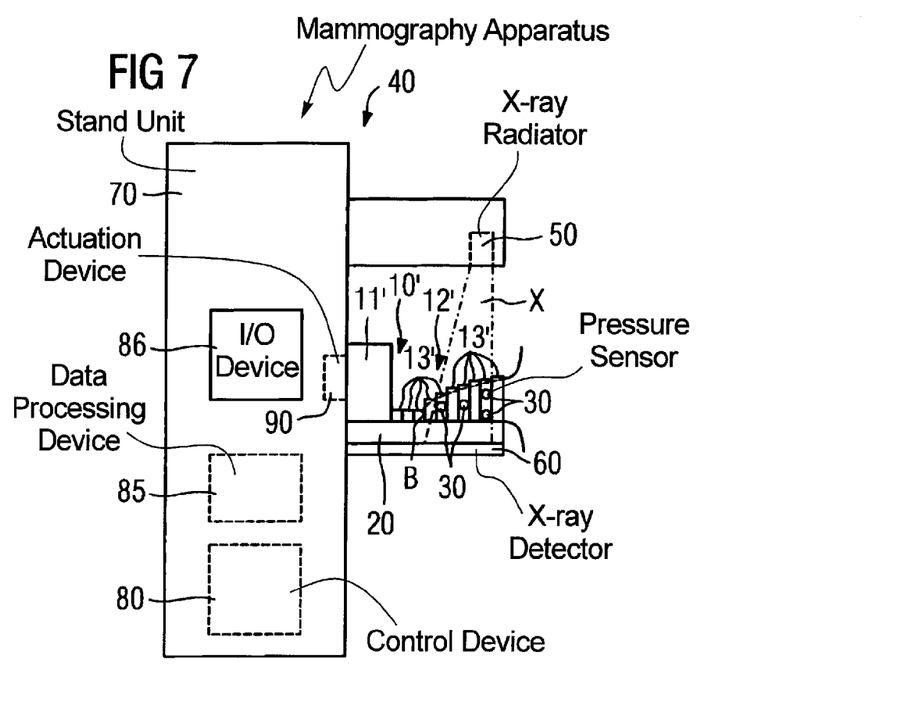
FIG. 7 is a side view of a mammography device with an inventive control device.

FIG. 7 shows a medical device which is fashioned as a mammography apparatus 40 during an x-ray exposure of a female breast B. For implementation of a mammography examination, compression of the female breast B is required, which is achieved with an inventive compression device 10'.

The mammography apparatus 40 has a stand unit 70 on which are arranged an x-ray radiator 50 and an x-ray detector 60 situated opposite the x-ray radiator 50 and aligned to the x-ray radiator 50. X-rays X are used for examination of the breast B, meaning that in the exemplary embodiment the examination field is the x-rays X. A support table 20 on which the subject (i.e. the female breast B) to be compressed is positioned during the examination is arranged between the x-ray radiator 50 and the x-ray detector 60.

The mammography apparatus 40 furthermore has a compression device 10' that includes a displacement device 11' and a compression plate 12'. The compression plate 12' has a number of elastically-deformable compression plate elements 13' that compress the female breast B dependent on its anatomy. The compressed state of the female breast B is shown in FIG. 7. A number of sensors 30 are embedded in the compression plate elements 13' for measurement of the compression pressure on the female breast B.

Furthermore, the mammography apparatus 40 has a control device 80 to which data are supplied (in a contact-free, cable-free manner) that are associated with the compression pressures measured by the sensors 30. The control device 80 is memory-programmable. The values supplied to the control device 80 for the measured compression pressure are compared with one value or a number of values that are stored in the control device 80, for example for a desired compression pressure and/or a limit value fixing a maximum of the compression pressure.

The control device 80 controls an actuation device 90 such that the value stored in the control device 80 is set for the desired compression pressure on the female breast B and the limit value for the compression pressure (that normally represents a maximum compression pressure) is not exceeded.

Furthermore, the mammography apparatus 40 has a data processing device 85 that determines a compression pressure distribution for the breast B from the data transmitted from the control device 80 to the data processing device 85 and associated with the measured compression pressure. For this purpose, a spatial association of the compression pressure values detected with the sensors 30 is effected. A spatial and, if applicable, temporal modification of the compression pressure distribution on the breast B is determined from the values by interpolation. The determined compression pressure distribution is output on an input/output (I/O) device 86, advantageously as a false color representation, with the magnitude ranges of the compression pressure being color-coded. This allows a quick recognition by medical personnel as to whether the compression pressure applied to the subject B has reached a critical value range that, for example, is coded with the color red. In the event that this is the case, the compression of the breast B can be stopped by the medical personnel.

Figure 8:
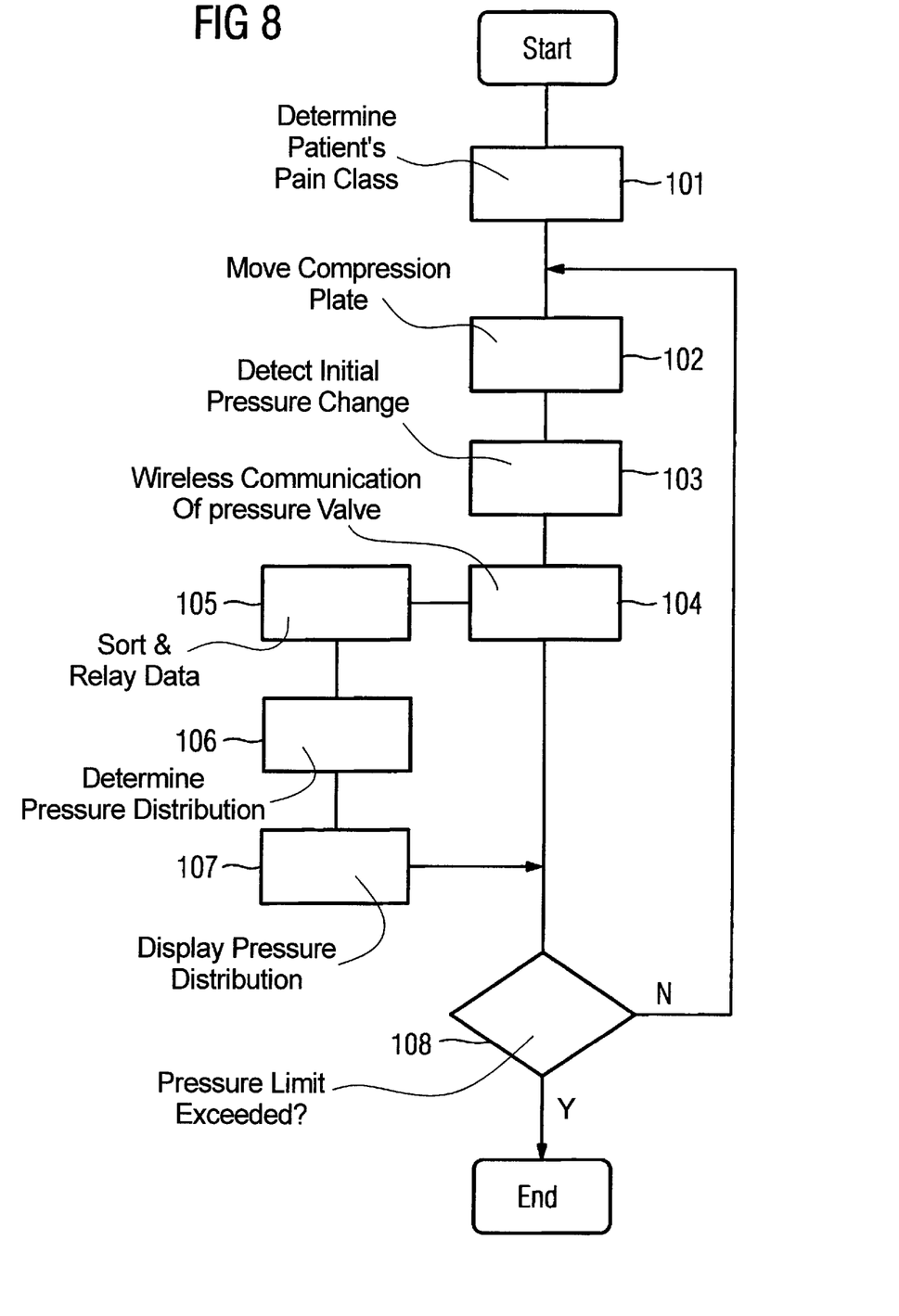
FIG. 8 is a flowchart for implementation of the inventive method.

FIG. 8 shows a flowchart for representation of the inventive method for adjustment of a compression pressure. The flowchart is explained in connection with the mammography apparatus 40 shown in FIG. 7, so reference characters of device components refer to FIG. 7.

In the explanation of the methods the following is assumed. A patient to receive a mammography examination is positioned standing at the mammography apparatus 40 such that her breast B is on the support table 20. The support table 20 as well as the breast B, are located between the x-ray radiator 50 and the x-ray detector 60. The x-ray radiator 50 is aligned to the x-ray detector 60.

In a first method step 101, a pain class is associated with the patient, for example by questioning, and an upper limit value for the compression pressure to be exerted on the breast B of the patient is determined via an input/output apparatus 86 at the mammography device 40. In the exemplary embodiment this limit value is equal to the desired compression pressure value in order to generate a sufficient compression of the breast B for the x-ray acquisition with the mammography apparatus 40. The determined limit value is stored in the control device 80.

The medical attendant starts the compression procedure for the breast B. In a method step 102 the compression device 10' is moved vertically in the direction of the bearing table 20 on which the breast B is arranged. The compression device 10' has a displacement device 11' that can be driven by means of a motor, on which displacement device 11' a compression plate 12' is arranged. The motorized actuation of the displacement device 11' ensues by means of an actuation device 90 controlled by the control device 90.

As soon as the compression plate 12' (which has a number of elastically-deformable compression plate elements 13') contacts the breast B, a counterforce directed against the movement of the displacement device 11' is generated. The compression plate elements 13' embody sensors 30 for measurement of the compression pressure. This initial change of the pressure is detected by a sensor 30 or a number of sensors 30 in a method step 103. A compression pressure value is associated with the respective compression pressure detected by the sensor 30 in the method step 103, this compression pressure value being communicated without contact from the sensors 30 to the control device 80 in a method step 104 with means (not shown) for contact-free transfer of data.

The control device 80 sorts the supplied compression pressure values and relays the sorted data to a data processing device 85 in a method step 105. There a compression pressure distribution for the breast B is calculated or determined from the detected compression pressures or data in a method step 106. The calculated compression pressure distribution is displayed on an input/output device 86 as a planar or spatial false-color representation of the breast B in a method step 107.

In a method step 108 the compression pressure values supplied without contact from the sensors 30 to the control device 80 are compared with the limit value stored in the control device 80 in the method step 101. If the limit value is greater than the compression pressure value with maximum compression pressure magnitude, a further displacement of the compression device 10' in the direction of the support table 20 ensues according to the method step 102. The breast B is further compressed i.e. the compression pressure is increased. The method step 108 can also ensue in parallel with the method steps 105, 106 and 107 which serve for the determination of a graphical representation of a compression pressure distribution on the compressed breast B.

According to the method step 103, the compression pressure generated at the respective sensor 30 is measured again and a data set associated with the measured compression pressure are supplied to the control device 80 via the means for contact-free transfer of data and energy according to method step 104. The representation of the compression pressure distribution is updated according to method steps 105, 106 and 107.

In method step 108 it is again compared whether the magnitude of the current compression pressure value for the breast B, that is measured after a further displacement of the compression device 10' in the direction of the support table 20, is less than the limit value stored in the control device 80 in the method step 101. If the stored limit value has still not yet been reached, a further displacement or compression of the breast B is affected until the limit value is reached.

If the limit value is exceeded by a measured compression pressure value, a reversal of the displacement direction of the compression device 10' thus ensues which is controlled by the control device 80 and is effected by the drive device 90 until all compression pressure values lie below the predetermined limit value. If applicable a further manual compression can be effected after consultation with the patient, insofar as this increases the examination success to be expected.

Radioscopy of the breast B with x-rays X subsequently ensues (possibly from a plurality of projection directions) in order to determine a spatial representation of the breast B.

Flexible compression plates adapting to the physical structure of a subject to be compressed are provided by the inventive compression device, the flexible compression plates—in contrast to rigid compression plates available today (for example made from polymethylmethacrylate (PMMA))—are free of structures that are visible in x-ray projections. Furthermore, the number of compression plates, as are required today to be provided, can be reduced by the inventive elastically-deformable compression plate having a number of elastically-deformable compression plate elements. In contrast to previous mammography systems, the compression pressure can be determined not only grossly via a compression arm but also directly at the compressed subject, dependent on the number of the sensors at arbitrary positions, from which a temporal and a spatial curve of a compression pressure distributions for the subject to be compressed can be determined.

The method and device can be used, for example, for diagnosis purposes of the breast of a woman in order to determine local pressure maxima (for instance caused by nodules) in the compressed state of the breast without exposing the breast to x-ray radiation.

Although modifications and changes may be suggested by those skilled in the art, it is the intention of the inventor to embody within the patent warranted hereon all changes and modifications as reasonably and properly come within the scope of his contribution to the art.

I claim as my invention:

1. A compression device for assisting examination of a subject using a field of penetrating radiation, comprising:
   a support plate configured to receive a subject thereon;
   a compression plate that is at least partially penetrated by radiation in said field and that is spaced from said support plate;
   a displacement device that modifies the spacing between said compression plate and said support plate to compress said subject between said compression plate and said support plate;
   said compression plate comprising a plurality of elastically-deformable compression plate elements that press against said subject to compress said subject; and
   said plurality of elastically-deformable compression elements being substantially transparent to said radiation.

2. A compression device as claimed in claim 1 wherein at least one of said compression plate elements is a solid-cylindrical body.

3. A compression device as claimed in claim 1 wherein at least one of said compression elements is a hollow-cylindrical body.

4. A compression device as claimed in claim 3 comprising a fluid source in communication with an interior of said hollow-cylindrical body, said fluid source supplying fluid to said interior of said hollow-cylindrical body to selectively adjust a pressure applied to said subject by said hollow-cylindrical body.

5. A compression device as claimed in claim 1 wherein at least one of said compression plate elements is comprised of a material having material properties that are substantially unaltered by interaction with said field.

6. A compression device as claimed in claim 5 wherein said material is plastic.

7. A compression device as claimed in claim 1 comprising at least one pressure sensor embodied in at least one of said compression plate elements that measures a pressure applied to said subject by said at least one of said compression plate elements.

8. A compression device as claimed in claim 7 wherein said at least one sensor comprises a transmission element for contact-free transfer of data from said pressure sensor and energy to said pressure sensor.

9. A compression device as claimed in claim 7 wherein said at least one sensor comprises a piezoelectric element that detects pressure applied by said at least one of said compression plate elements to said subject.

10. A compression device as claimed in claim 7 wherein said at least one sensor comprises a pyroelectric element that detects pressure applied by said at least one of said compression plate elements to said subject.

11. A compression device as claimed in claim 1 comprising a plurality of pressure sensors carried by at least one of said compression plate elements, said plurality of pressure sensors being respectively disposed at different positions and orientations on said at least one compression plate element, and pressure applied by said at least one compression plate element to said subject.

12. A compression device as claimed in claim 1 wherein at least one of said compression plate elements is configured to apply a modifiable pressure to said subject, and comprising a pressure sensor that detects a pressure applied by said at least one of said compression plate elements to said subject, and a control unit supplied with an output from said pressure sensor that modifies said pressure applied to the subject by said at least one of said compression plate elements dependent on the pressure detected by said pressure sensor.

13. A compression device as claimed in claim 1 wherein said at least one of said compression plate elements is mounted in said compression plate so as to exhibit a modifiable tension, and wherein said control unit modifies said tension to modify said pressure applied by said at least one of said compression plate elements to said subject.

14. A compression device as claimed in claim 1 wherein said compression plate and support plate are configured to receive a female breast therebetween, as said subject, and to compress the female breast between the compression plate and the support plate.

15. A mammography apparatus comprising:
   a support plate configured to receive a female breast thereon;
   a compression plate spaced from said support plate;
   displacement device that modifies the spacing between said compression plate and said support plate to compress the female breast between the compression plate and the support plate;
   an x-ray imaging system that emits x-rays that proceed through said compression plate to obtain an x-ray image of the female breast; and
   said compression plate comprising a plurality of elastically-deformable compression plate elements that contact the female breast as said spacing is modified, to apply pressure to the female breast on the support plate to compress the female breast on the support plate, said elastically-deformable compression plate elements being substantially transparent to said x-rays.

16. A mammography apparatus as claimed in claim 15 comprising:
   at least one pressure sensor embodied in at least one of said elastically-deformable compression plate elements that detects a pressure applied by said at least one of said elastically-deformable elements to the female breast and that emits a sensor output representing the detected pressure; and
   a control unit in communication with said at least one pressure sensor via a communication link, said control unit controlling operation of said displacement device dependent on said sensor output.

17. A mammography apparatus as claimed in claim 16 wherein said control unit compares said sensor output to a compression pressure value stored in said control unit and controls said displacement device to maintain pressure applied to the female breast by said at least one of said elastic compression plate elements at said compression pressure value.

18. A mammography apparatus as claimed in claim 16 wherein said communication link is a wireless communication link.

19. A mammography apparatus as claimed in claim 15 wherein said compression plate comprises a rigid plate element having an opening therein extending from one side of said rigid plate element, said opening being configured to surround the female breast, and wherein said plurality of elastically-deformable compression plate elements are respectively mounted to said rigid plate element so as to span said opening.

* * * * *